United States Patent [19]

Feldman

[11] 4,359,593
[45] Nov. 16, 1982

[54] PROCESS FOR RECOVERING ETHANOL FROM DILUTE AQUEOUS SOLUTIONS EMPLOYING SOLID SORBENT

[75] Inventor: Julian Feldman, Cincinnati, Ohio

[73] Assignee: National Distillers & Chemical Corp., New York, N.Y.

[21] Appl. No.: 325,450

[22] Filed: Nov. 27, 1981

[51] Int. Cl.³ .................................................. C07C 29/76
[52] U.S. Cl. ..................................... 568/916; 568/917
[58] Field of Search ............................. 568/916, 917

[56] References Cited

U.S. PATENT DOCUMENTS

| | | | |
|---|---|---|---|
| 2,943,105 | 6/1960 | Caruthers | 568/917 |
| 3,021,374 | 2/1962 | Radzitzki | 568/917 |
| 3,485,879 | 12/1969 | Mameniskis et al. | 568/917 |
| 4,277,635 | 7/1981 | Oulman et al. | 568/916 |

*Primary Examiner*—Joseph E. Evans
*Attorney, Agent, or Firm*—Kenneth D. Tremain

[57] ABSTRACT

Ethanol is recovered from a dilute aqueous stream thereof by contacting said stream with crosslinked polyvinylpyridine resin or nuclear substituted derivative thereof to effect selective sorption of the ethanol by said resin. Sorbed ethanol is thereafter removed from the resin by stripping with an inert gas such as carbon dioxide.

11 Claims, 4 Drawing Figures

PROCESS FOR RECOVERING ETHANOL FROM DILUTE AQUEOUS SOLUTIONS EMPLOYING SOLID SORBENT

BACKGROUND OF THE INVENTION

1. Field of the Invention

This invention relates to the recovery of ethanol from dilute aqueous solutions by selective sorption and is especially applicable to the dilute aqueous ethanol obtained from fermentation.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity consumed and versatility in product synthesis.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentation of sugar to a dilute solution of ethanol ("beer") and the separation and concentration of the ethanol by distillation, have been modified in numerous ways to achieve improvements in product yield, production rates and so forth (see, for example, U.S. Pat. No. 3,236,740 and the booklet "Industrial Alcohol by Continuous Fermentation and Vacuum Distillation With Low Energy Consumption," of Chemapec, Inc., Woodbury, N.Y.). For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol produced and enhance the standing of the ethanol as an economically viable replacement for petroleum based raw materials. To date, however, relatively little concern has been given to the energy and raw material requirements for manufacturing ethanol from biomass and consequently, little effort has been made to minimize the thermal expenditure and waste of raw materials incurred in carrying out any of the aforesaid discrete operations involved in the manufacture of ethanol from vegetative sources.

Recovery of fermentation ethanol by distillation accounts for a large amount of the overall energy requirements for conversion of biomass to concentrated ethanol. Berry, "Distribution of Ethanol-Water Mixtures to Organic Liquids" *Ind. Eng. Process Des. Dev.* 1981, 20, 104–108 describes attempts to use solvent extraction as a substitute for distillation in alcohol separation and concentration. According to this publication, the hydrocarbons as a class are poor extractants for ethanol, but tend to give the highest separation factors because of their even poorer solvent properties for water. A variety of solvents, each of them liquid, are evaluated in this publication including cyclohexane, benzene, toluene, xylene, ethybenzene, chloroform, 1-octanol, n-butyl acetate and tri-n-butyl phosphate.

While it is known from Japanese Patent Publication No. J50639-025 that crosslinked polyvinylpyridine resin is useful for separating phenolic compounds such as phenol, cresol, ethylphenol, naphthol, catechol, resorcinol, hydroquinone or their derivatives, there is no suggestion in this disclosure that resins of this type may also be useful for the preferential adsorption of ethanol from a dilute aqueous ethanol stream.

SUMMARY OF THE INVENTION

It has now been discovered that ethanol can be readily separated and concentrated from a dilute aqueous solution thereof by the process which comprises contacting said dilute aqueous ethanol solution with crosslinked polyvinylpyridine resin or nuclear derivative thereof under such conditions that at least a portion of the ethanol present in the solution will be sorbed by said resin.

To remove the sorbed ethanol from the crosslinked polyvinylpyridine sorbent, it is within the scope of the present invention to use an inert stripping gas such as carbon dioxide at an elevated temperature.

The use of crosslinked polyvinylpyridine resin possesses several practical advantages over the use of a liquid ethanol solvent as proposed by Roddy, supra. Use of an organic solvent to extract ethanol from an aqueous solution necessarily results in two liquid phases, an organic phase containing ethanol and an aqueous phase. These two phases must be separated prior to recovering the ethanol from the organic phase, e.g., by stripping with inert gas. However, by employing a solid ethanol sorbent as in the present invention, there is no necessity to separate two liquid phases and the ethanol sorbed by the crosslinked polyvinylpyridine can be periodically removed therefrom merely by stripping with inert gas. Moreover, stripping ethanol dissolved in a liquid solvent using a gas poses the disadvantage that some solvent will also be stripped by the gas and will be in admixture with the ethanol product. However, gas stripping of a solid sorbent to effect ethanol removal presents no such problem.

While the advantages of the process of this invention are especially realized when applied to the recovery of ethanol from a fermentation product stream, it is also of benefit in recovering ethanol from dilute aqueous media resulting from other processes, e.g., the dilute ethanol obtained by the catalytic hydration of ethylene.

DESCRIPTION OF THE PREFERRED EMBODIMENTS

The useful crosslinked polyvinylpyridine sorbents herein include those prepared from 2-, 3- or 4-vinylpyridine, the nuclear substituted derivatives thereof, for example, those in which any and up to all of the nuclear hydrogens are substituted with such groups as halo, lower alkyl, lower alkoxy, nitro, amino, etc., and combinations of the foregoing vinyl monomers. Crosslinking of poly(4-vinylpyridine) can be effected by reacting the polymer with a compound having at least two acidic sites, e.g., 1,2-ethylene dichloride, 1,2-ethylene dibromide, polysulfonated vinyl benzene and divinyl benzene, etc. A particularly preferred sorbent is crosslinked poly(4-vinylpyridine) which is commercially available. Typical properties of such sorbent, Reilly Tar & Chemical Corporation R8050 crosslinked poly(4-vinylpyridine), are as follows:

| Property | |
| --- | --- |
| Appearance | Off-white to tan granular solid |
| Bulk density, g/mL | 0.45 |
| lb/ft$^3$ | 28 |
| Skeletal density, g/cm$^3$ | 1.154 |
| Moisture, % by weight | |
| dry | 0.5% to 2.0% |
| wet | 36–39% |
| Apparent pKa | 5.8 |
| Hydrogen ion capacity, meq/g based on dry polymer | |
| in water | 8.8 |
| in toluene | 8.5 |
| Percentage swelling from free base to hydrochloride form, in water | 100% |
| Percentage swelling from dry state to solvent-saturated state | |
| methanol | 70–75% |
| acetone | 30–35% |
| water | 33–37% |
| isopropanol | 13–17% |
| toluene | 8–12% |
| ethyl acetate | 3–6% |
| hexane | 0% |
| Temperature stability | >100° C. |

Figure 1:
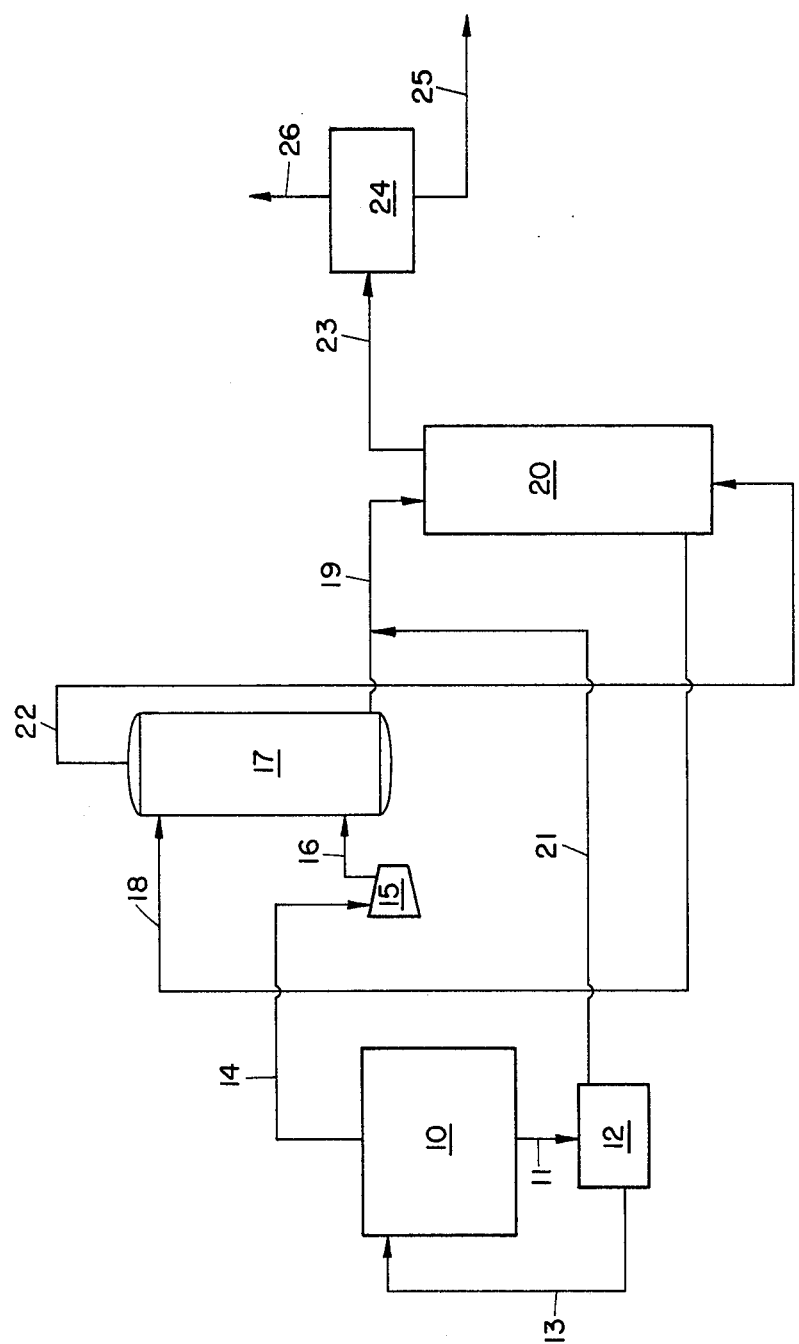
FIG. 1 is flow diagram of one embodiment of the ethanol recovery process herein applied to a dilute aqueous ethanol stream obtained from fermentation.

In accordance with FIG. 1, a dilute aqueous ethanol solution, e.g., one containing from about 2–12 weight percent ethanol, produced in fermentation zone 10 by the action of yeast on a sterile aqueous solution of fermentable sugar(s) is transferred through line 11 to yeast separation zone 12, the thick slurry of recovered yeast being recycled to the fermentation zone through line 13 and the substantially yeast-free ethanol stream being conveyed through line 21 to be combined with dilute aqueous ethanol recovered from carbon dioxide as hereinafter described. Fermentation in zone 10 produces large quantities of metabolically evolved carbon dioxide gas containing small quantities of ethanol. The gaseous carbon dioxide/ethanol mixture is conveyed through line 14 and by means of blower 15 is introduced through line 16 into the bottom of ethanol adsorption unit 17. Recycle water at ambient temperature entering the top of adsorption unit 17 through line 18 and flowing downwardly therethrough adsorbs substantially all of the ethanol vapor rising through the unit. The dilute aqueous solution of ethanol withdrawn from the base of ethanol adsorption unit 17 through line 19 is combined with the yeast-free dilute aqueous ethanol stream in line 21 and the combined streams are fed into sorption zone 20 containing particulate crosslinked poly(4-vinylpyridine) resin. The particle size of the resin is not critical, the smaller particle sizes being preferred for the reason that the efficiency of sorption is related in part to the available surface area of the resin. In general, average particle sizes of from about 20 to about 300 mesh, and preferably, from about 40 to about 150 mesh provide good results. The quantities of resin employed can vary widely with optimum quantities being determined for a given system by taking into account such factors as the level of concentration of ethanol in the feed, the volume of the feed and its flow rate, the temperatures of the feed and sorption zone 20, contact time of the ethanol feed with the sorbent resin and similar factors as will be readily understood by those skilled in the art. While the embodiment of the invention shown illustrates the use of carbon dioxide recovered from ethanol adsorption unit 17 through line 22 to strip ethanol sorbed on the resin in sorption zone 20, it is to be understood that any other gas inert to ethanol, e.g., nitrogen, air, steam, etc., can also be used for this purpose. The gas is preferably heated prior to introduction into sorption zone 20 to increase the rate of desorption of the sorbed ethanol. Ordinarily, sorption zone 20 will be operated in alternate sorption-desorption modes for the sake of optimum efficiency. The volumes of gas passed through sorption zone 20 to effect desorption of ethanol are also subject to considerable variation, it generally being desirable to use only so much gas as is required to maintain a predetermined level of desorption. The gaseous ethanol stream recovered from sorption zone 20 through line 23 and containing some water vapor is introduced into condenser 24, the condensed aqueous ethanol, now at a substantially higher ethanol concentration than the ethanol stream feed, being discharged from the system through line 25 and the gaseous carbon dioxide being vented to the atmosphere through line 26.

The following example is further illustrative of the process of this invention:

EXAMPLE 1

Four samples, A, B, C and D of 20 ml each, and a fifth sample, E, of 30 ml obtained from an aqueous solution of anhydrous ethanol having a volumetric ratio of water to ethanol of 10:1 contained varying amounts of crosslinked poly(4-vinylpyridine) as follows:

| Ethanol Solution | Sorbent Resin, grams | Grams of Sorbent Resin/Ml of Ethanol |
| --- | --- | --- |
| A | 0.5 | 0.025 |
| B | 1 | 0.05 |
| C | 2 | 0.10 |
| D | 4 | 0.20 |
| E | 10 | 0.33 |

The samples were left standing for approximately 12–18 hours after which the aqueous fractions were analyzed by gas chromatography employing simple area comparison techniques. A 6' glass column packed with Chromosorb 102 silica gel at 180° C. isothermal, 58 psi helium pressure and 30 cc/min helium flow was employed for the analysis. The sample size was 0.6 ml in each case.

The results of the analysis were as follows:

| Aqueous Fraction Following Sorption Of Ethanol | Ethanol Count | Average Counts | Weight Percent of Original Ethanol Present in Aqueous Fraction |
|---|---|---|---|
| Control* | 92,563 | 91,781 | — |
|  | 91,736 |  |  |
|  | 91,044 |  |  |
| A | 87,870 | 88,247 | 96.15% |
|  | 88,624 |  |  |
| B | 86,186 | 86,603 | 94.35 |
|  | 87,021 |  |  |
| C | 85,447 | 85,910 | 93.60 |
|  | 86,373 |  |  |
| D | 84,954 | 82,075 | 89.40 |
|  | 79,197 |  |  |
| E | 64,153 | 69,045 | 75.23 |
|  | 73,577 |  |  |

*Aqueous fraction of sample A after 3 hours of settling.

As these data show, significant levels of ethanol sorption were observed after only a few hours of contact time with the sorbent resin, the extent of sorption being increased as the amount of resin employed increased.

EXAMPLE 2

Small weighed portions of crosslinked poly(4-vinylpyridine) resin were equilibrated with 1.0 ml quantities of an 8% solution of ethanol in water. The concentrations of ethanol in the equilibrated solutions at room temperature were determined by injecting equal volumes of supernatant solution into a gas liquid chromatograph with the following results:

| Adsorption of Ethanol from 1.0 ml Solution of Aqueous Ethanol ||||
|---|---|---|
| Wt. of Resin gms | Equilibrium Conc. of Ethanol, % | Relative Adsorbability gm Alcohol/gm Resin |
| 0 | 8.0 | — |
| .025 | 7.70 | 0.128 |
| .05 | 7.55 | 0.096 |
| .10 | 7.49 | 0.051 |
| .20 | 7.15 | 0.042 |
| .33 | 6.02 | 0.060 |

EXAMPLE 3

Figure 2:
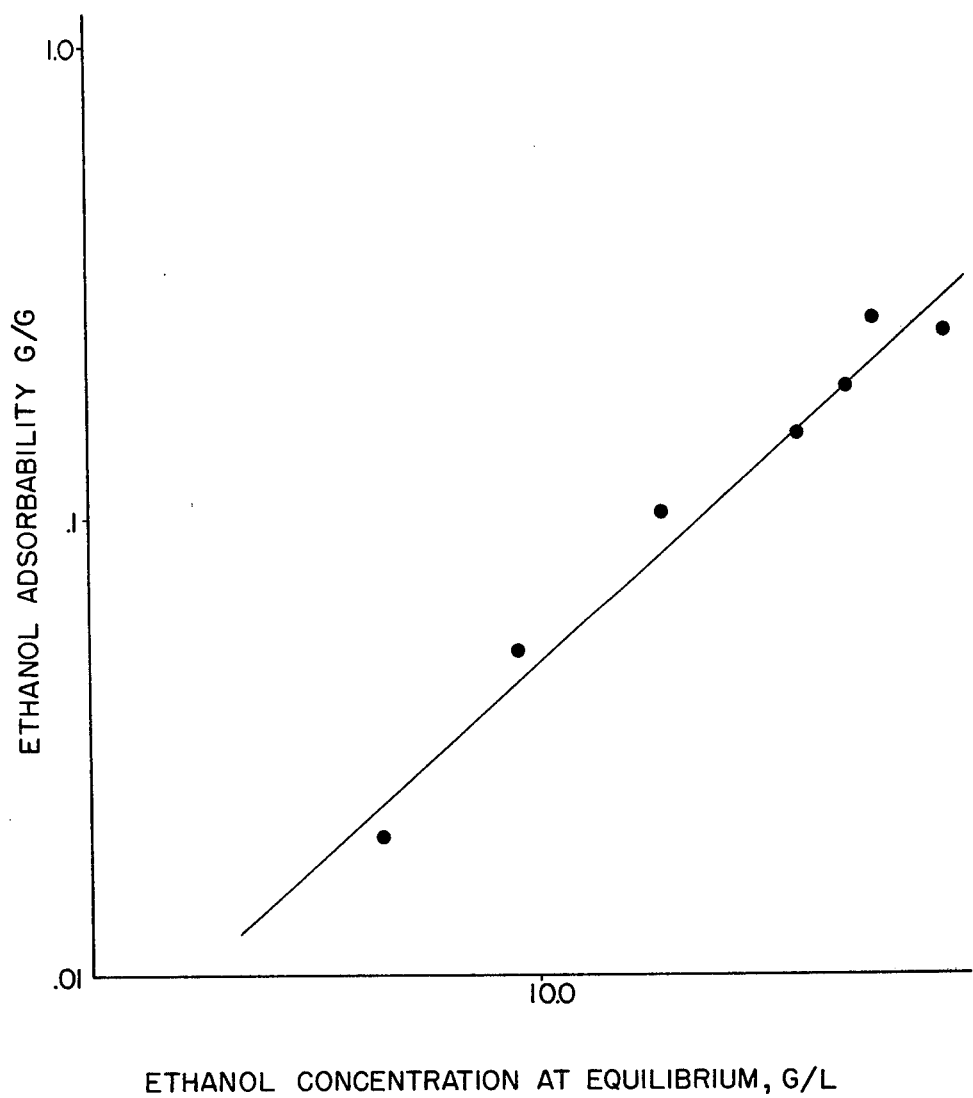
FIG. 2 is a curve of the adsorption isotherm relative for ethanol from water on crosslinked poly(4-vinylpyridine) resin measured at 22° C.

The relative adsorption isotherm for ethanol from water on crosslinked poly(4-vinylpyridine) resin at ambient temperature was determined over the concentration range of 0.55 to 11% ethanol and is plotted in FIG. 2. The experiments were conducted by equilibrating 0.25 g portions of resin with 10 ml volumes of aqueous ethanol of various concentrations. The mixtures were allowed to stand for 18 hours with occasional stirring. Analysis was made by introducing an internal standard into an aliquot portion of the supernatant liquid and injecting into a gas liquid chromatographic apparatus. The relative amount of ethanol adsorbed was determined from the difference between the initial concentration and the final concentration. At concentrations above 5%, it was found that longer equilibration times were required and that a maximum adsorption of 0.33 g alcohol/gm resin was obtained at 10.1% alcohol concentration.

In the examples given above, it is to be understood that water is also adsorbed so that the values reported show relative adsorption and are not to be taken as absolute values. The absolute adsorptive capacity of poly(4-vinylpyridine) resin for various situations has been determined by vapor phase equilibration with the results appearing in the following table. Capacity appears to be related to the activity of the hydroxylic hydrogen.

TABLE IV-1

| PERCENT ADSORPTION AT 25° C. ||||
|---|---|---|---|
|  | On Polyvinylpyridine | On PCB Granular C | On PGL Powder C |
| Water | 33 | 45 | 57 |
| Methanol | 92 | 38 | 48 |
| Ethanol | 80 | 35 | 49 |
| Isopropanol | 40 | 34 | 45 |
| Tert-Butanol | 19 | 35 | 49 |
| Acetic Acid | 295 | 81 | 90 |
| Ethyl Acetate | 4.9 | 43 | 73 |
| Carbon Tetrachloride | 0.8 |  |  |

EXAMPLE 4

In this example, the absolute adsorption isotherms for ethanol in a solvent which is not adsorbed on crosslinked poly(4-vinylpyridine) resin, namely, carbon tetrachloride, were measured at three temperatures: 5° C., 30° C., and 60° C. The experiments were performed by equilibrating a known amount of dried resin in a 15 ml reaction bottle capped with a teflon lined silicone septum held in place by a crimped-on aluminum cap. (Pierce Chem. Co., Rockford, Ill., Cat. Nos. 12911, 12813 and 13213, respectively.) The resin was added to the empty vials, which were then capped and reweighed. The liquids were added by syringe through the septa. The bottles were suspended by wires from a horizontal bar running across the top of a 5 gal. thermostat equipped with a calrod heater and a freon compressor (Wilkens Anderson-LO temp. bath). A mercury thermoregulator and stirrer held the temperature to within ±0.1° C. Enough slack on the wires was present to allow the bottles to be removed from the bath and shaken vigorously, which was done at intervals of 15 minutes or so for periods of approximately 5 seconds. The resin rose to the top of the mixture. After settling to clear, the needle of a 10 microliter Hamilton syringe was inserted through the septum, flushed 8 to 10 times and a 1 microliter sample withdrawn for analysis in a Varian 1200 chromatograph. Using a 10 ft long column containing 20% FFAP (free fatty acid phase) on chromosorb W/AW 80-100 mesh, DMS treated, at an oven temp. of 60° C., injector temp. of 190° C. and a flame-ionization detector at 230° C. with a helium flow of 20 ml/min., an Autolab System IV-electronic digital integrator was used to obtain peak areas and report the results in terms of area %. At these conditions, the carbon tetrachloride emerged at 298 seconds and the ethanol at 380 seconds with just enough separation to provide sharply resolved peaks. Since the detector response was not linear, a calibration curve was constructed from mixtures of ethanol and carbon tetrachloride which plotted area % against composition. The compositions of the equilibrium mixtures C were determined in this manner. These compositions were used to determine the weight of ethanol A, in the equilibrium mixture by using the equation.

$$A = \frac{CCl_4 \times \% C}{(100 - \% C)}$$

wherein CCl₄ is the weight of carbon tetrachloride in the sample and % C is the composition in ethanol % of the equilibrium mixture as determined by the GLC method described above.

Figure 3:
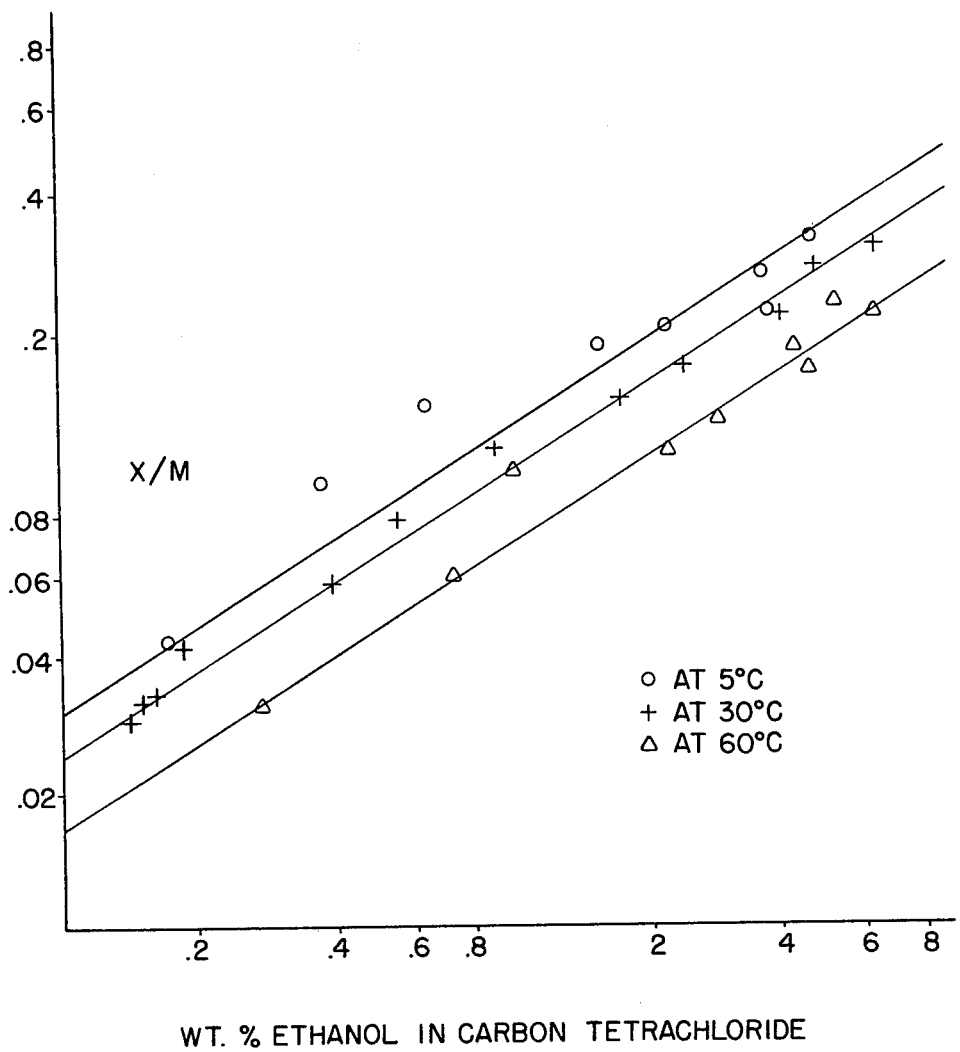
FIG. 3 are curves of the absolute adsorption isotherm for ethanol from carbon tetrachloride on crosslinked poly(4-vinylpyridine) resin measured at 5°, 30° and 60°.

The value of A was then subtracted from the weight of ethanol in the original mixture to give the weight of ethanol X adsorbed by the resin. The values X/M where M is the weight of the resin were plotted against the equilibrium concentration C on log paper to give the Freundlich isotherms shown in FIG. 3. These isotherms are linear up to compositions of 5% ethanol and have paralled slopes equal to 0.62. The intercept values for the constant K in the Freundlich isotherms were linear with respect to the temperature so that the following equation can be used in the ranges of concentration and temperature studied to relate the adsorbability of ethanol on poly(4-vinylpyridine):

$$X/M = (1220 - 9.09t)10^{-4}C^{0.62}$$

wherein X is the weight of ethanol in gms adsorbed on M gms of resin at t° C. and C is the weight % of ethanol in the equilibrated solution.

EXAMPLE 5

This example derives the relative adsorption isotherms of aqueous ethanol at varying temperatures. Example 4 was repeated using mixtures of ethanol and water at the same three temperatures, 5° C., 30° C., and 60° C. The procedure was essentially identical except for the analysis. Since water is not detected by flame ionization, n-propanol was used as an internal standard. Thus, a solution of known concentration of propanol in water was prepared and stored in a serum capped vial (approx. 9%). A small quantity (approx. 0.3 ml) of this solution was withdrawn and injected into a tared 4 ml vial which was immediately capped and weighed. Approximately 0.2 ml of supernatant liquid was withdrawn from the equilibrated sample bottle through the septum and added quickly to the vial which was immediately capped and weighed. Duplicate analyses were then run on this thoroughly mixed sample by injecting 1 μl into the gas chromatograph. In this case the oven temperature was 80° C. with the same column and gas flow as used in Example 4. Retention times were 225 secs. for ethanol and 390 secs. for propanol.

After each run, the bottles containing the crosslinked poly(4-vinylpyridine) resin adsorbent were removed from the bath, dried and reweighed. The weight loss ranged from 140 mgms to 260 mgms after the run at 5° C. and from 180 mgms to 350 mgms after the 30° C. experiment with one showing almost a 1 gm loss. The liquids content of the bottles and the quantity of ethanol lost were corrected for by assuming the loss was of the liquid only at the concentration of ethanol determined from the previous run.

Figure 4:
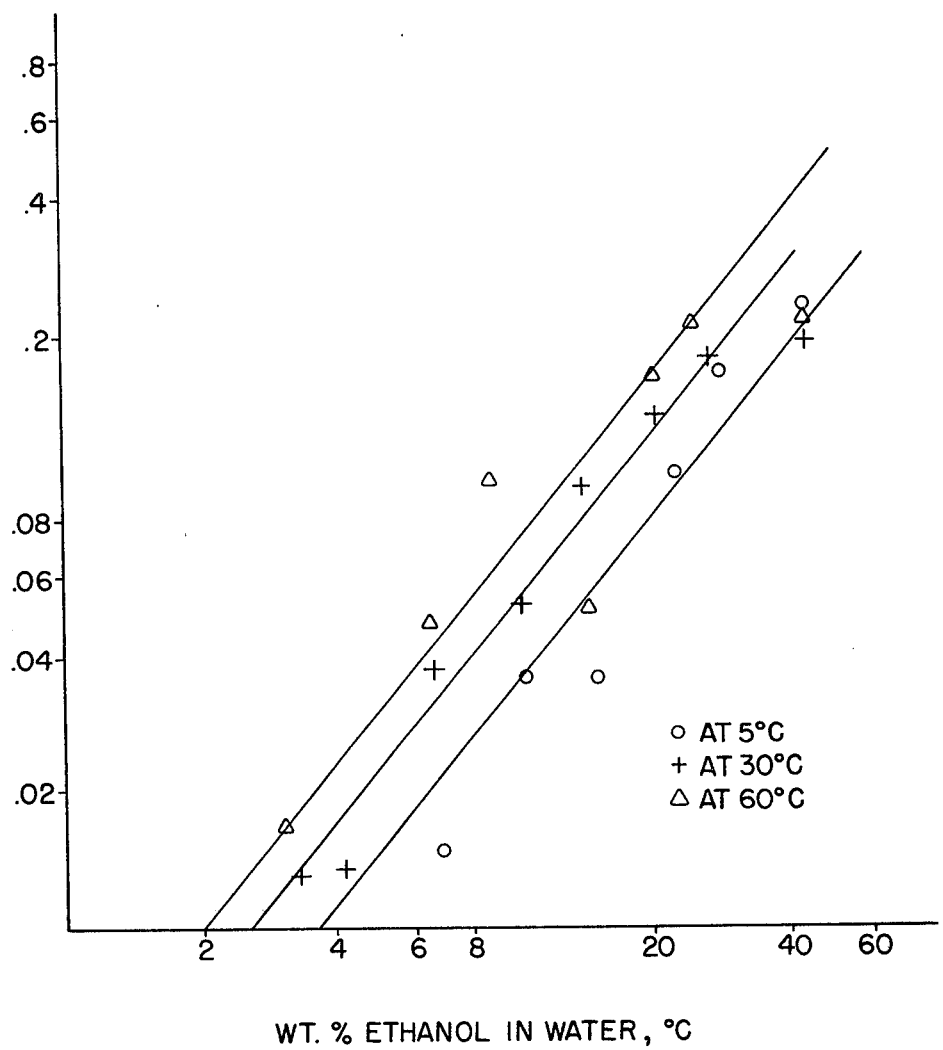
FIG. 4 are curves of the relative adsorption isotherm for ethanol from water on crosslinked poly(4-vinylpyridine) resin measured at 5°, 30° and 60° C.

The ethanol content was determined by GLC analysis as described in Example 4 and the values were calculated from a calibration curve made from known concentrations of ethanol and propanol mixtures. The results appear in the table below and the values of the relative amount of ethanol adsorbed per gm of resin are plotted against the equilibrium concentrations to give the Freundlich isotherms shown in FIG. 4. As in Example 3, there is almost a linear dependence of the intercept constant on temperature so that the equation for the relative adsorption isotherm for ethanol from aqueous solution is $$X/M = (200 + 3.33t)10^{-5}C^{1.23}$$

in the temperature range of 5° to 60° C. and equilibrium concentrations of 3-30% ethanol, where the symbols are the same as before.

The major difference between these isotherms and those obtained in carbon tetrachloride is that the latter have a lesser dependence on the concentration and show decreasing adsorption with increasing temperature whereas the aqueous solution shows an increase in relative adsorption with increasing temperature. This may be interpreted as indicating less adsorption of water with increase in temperature. Thus, separation of ethanol from water should be favored by adsorption with crosslinked poly(4-vinylpyridine) resin at higher temperatures.

TABLE

ADSORPTION OF ETHANOL FROM AQUEOUS SOLUTIONS ON CROSSLINKED POLY(4-VINYLPYRIDINE)

| m, gms Resin | a. Aq. Propanol gms | b. Propanol gms × 10² | c. GLC Value, % | d. Ethanol % | e. Sample gms | f. Equilibrium Concentration Ethanol, % | g. Liquids gms | h. Liquids Lost gms | j. Ethanol Lost mgms | k. Ethanol In Solution gms | x. Rel. Ethanol Adsorbed mgms | x/m × 10² |
|---|---|---|---|---|---|---|---|---|---|---|---|---|
| at 5° C. | | | | | | | | | | | | |
| 2.0520 | .2394 | 2.1153 | 16.485 | 19.2 | .154 | 3.26 | 10.6893 | | | .3648 | 16.3 | .79 |
| 2.1008 | .3575 | 3.1588 | 16.055 | 18.9 | .1063 | 6.93 | 10.3259 | | | .7461 | 30.5 | 1.45 |
| 1.8798 | .3257 | 2.8778 | 21.777 | 25.4 | .0941 | 10.41 | 10.8808 | | | 1.2006 | 67.9 | 3.61 |
| 1.8729 | .3463 | 3.0598 | 40.363 | 48.5 | .1978 | 14.57 | 10.4404 | | | 1.5871 | 65.9 | 3.52 |
| 1.9301 | .5735 | 5.0673 | 31.922 | 31.2 | .1393 | 21.55 | 8.4868 | | | 2.0232 | 194.3 | 10.07 |
| 1.8301 | .2868 | 2.5341 | 47.298 | 55.2 | .1129 | 27.66 | 9.6706 | | | 2.9697 | 294.8 | 16.11 |
| 1.8291 | .4563 | 4.0318 | 52.595 | 60.3 | .1515 | 40.42 | 8.6360 | | | 3.9283 | 437.6 | 23.92 |
| at 30° C. | | | | | | | | | | | | |
| 2.0520 | .2500 | 2.2089 | 17.670 | 20.5 | .1792 | 3.18 | 10.5128 | .1765 | 5.61 | .3592 | 24.9 | 1.21 |
| 2.1008 | .2146 | 1.8909 | 32.997 | 38.7 | .1839 | 6.49 | 10.1785 | .1473 | 9.56 | .7365 | 75.9 | 3.61 |
| 1.8798 | .2292 | 2.0252 | 39.740 | 46.5 | .1737 | 10.13 | 10.7243 | .1565 | 15.85 | 1.1848 | 98.4 | 5.24 |
| 1.8729 | .2615 | 2.3106 | 42.554 | 49.5 | .1666 | 13.59 | 10.1782 | .2622 | 35.63 | 1.5515 | 168.3 | 8.99 |
| 1.9301 | .3638 | 3.2145 | 43.703 | 51.0 | .1605 | 20.85 | 8.3205 | .1663 | 34.67 | 1.9885 | 253.6 | 13.14 |
| 1.8301 | .4563 | 4.0318 | 47.158 | 55.0 | .1803 | 27.33 | 9.5316 | .1390 | 37.99 | 2.9317 | 326.7 | 17.85 |
| 1.8291 | .5086 | 4.4939 | 46.716 | 54.3 | .1292 | 41.33 | 8.4512 | .1788 | 73.90 | 3.8544 | 359 | 19.63 |
| at 60° C. | | | | | | | | | | | | |
| 2.0520 | .1543 | 1.3634 | 23.723 | 27.7 | .1684 | 3.10 | 10.2230 | .2898 | 8.98 | .3502 | 33.3 | 1.62 |
| 2.1008 | .2325 | 2.0543 | 30.322 | 35.6 | .1807 | 6.28 | 9.8312 | .3473 | 97.3 | .7147 | 97.3 | 4.63 |
| 1.8798 | .2390 | 2.1118 | 37.351 | 43.8 | .1721 | 9.56 | 10.4668 | .2575 | 24.62 | 1.1601 | 159.5 | 8.49 |
| 1.8729 | .3187 | 2.8160 | 40.161 | 48.4 | .1892 | 13.96 | 9.4688 | .9716 | 135.63 | 1.4158 | 94 | 5.02 |
| 1.9301 | .2052 | 1.8131 | 57.022 | 65.0 | .1659 | 20.30 | 8.0523 | .2682 | 54.44 | 1.9341 | 299.5 | 15.52 |
| 1.8301 | .2668 | 2.3574 | 57.027 | 65.0 | .1647 | 26.58 | 9.2968 | .2348 | 62.41 | 2.8693 | 398.2 | 21.76 |

TABLE-continued
ADSORPTION OF ETHANOL FROM AQUEOUS SOLUTIONS ON CROSSLINKED POLY(4-VINYLPYRIDINE)

| m, gms Resin | a. Aq. Propanol gms | b. Propanol gms × 10² | c. GLC Value, % | d. Ethanol % | e. Sample gms | f. Equilibrium Concentration Ethanol, % | g. Liquids gms | h. Liquids Lost gms | j. Ethanol Lost mgms | k. Ethanol In Solution gms | x. Rel. Ethanol Adsorbed mgms | x/m × 10² |
|---|---|---|---|---|---|---|---|---|---|---|---|---|
| 1.8291 | .4031 | 3.5617 | 56.622 | 64.5 | .1592 | 40.65 | 8.2776 | .1796 | 73.01 | 3.7814 | 416.6 | 22.78 |

$b = a - 0.088358$ $f = \frac{d}{100 - d} \cdot \frac{b}{e} \cdot 100$ $x = k - fg$ $j = hf$

What is claimed is:

1. A process for recovering ethanol from a dilute aqueous solution thereof which comprises contacting said dilute aqueous ethanol stream with crosslinked polyvinylpyridine resin or nuclear substituted derivative thereof under such conditions that at least a portion of the ethanol will be sorbed by said resin and thereafter desorbing ethanol from said resin.

2. The process of claim 1 wherein the dilute aqueous solution of ethanol is obtained from fermentation.

3. The process of claim 2 wherein the dilute aqueous solution contains from about 2–12 weight percent ethanol.

4. The process of claim 1 wherein the crosslinked polyvinylpyridine is crosslinked poly(4-vinylpyridine).

5. The process of claim 1 further comprising the step of desorbing the ethanol employing an inert gas.

6. The process of claim 5 wherein the inert gas is carbon dioxide.

7. The process of claim 1 wherein the process is carried out at elevated temperature thereby increasing relative adsorption of crosslinked polyvinylpyridine for ethanol.

8. The process of claim 7 wherein the crosslinked polyvinylpyridine is crosslinked poly(4-vinylpyridine).

9. The process of claim 5 wherein ethanol is desorbed at elevated temperature.

10. The process of claim 6 wherein ethanol is desorbed with carbon dioxide at elevated temperature.

11. A process for recovering ethanol from a fermentation vessel at a concentration which is higher than the concentration of the ethanol in the fermentation medium which comprises:
   (a) contacting fermentation ethanol present in the dilute aqueous stream from the fermentation vessel with crosslinked polyvinylpyridine resin or nuclear substituted derivative thereof to sorb a significant percentage of the ethanol present in said stream;
   (b) employing the aqueous stream which has been contacted with the resin to adsorb ethanol present in the gaseous carbon dioxide stream produced in the fermentation vessel in an adsorption zone;
   (c) combining the dilute aqueous ethanol resulting from step (b) with the fermentation ethanol stream of step (a); and,
   (d) desorbing ethanol sorbed in step (a) with substantially ethanol-free carbon dioxide obtained from the adsorption zone of the step (b).

* * * * *